United States Patent [19]

Möller et al.

[11] Patent Number: 4,493,823

[45] Date of Patent: Jan. 15, 1985

[54] TOPICAL COSMETIC PREPARATIONS FOR THE TREATMENT OF OILY HAIR AND SEBORRHEIC SKIN

[75] Inventors: Hinrich Möller; Siegfried Wallat, both of Monheim; Friedhelm Bartnik; Wolfgang Pittermann, both of Düsseldorf, all of Fed. Rep. of Germany

[73] Assignee: Henkel Kommanditgesellschaft auf Aktien, Düsseldorf-Holthausen, Fed. Rep. of Germany

[21] Appl. No.: 319,915

[22] Filed: Nov. 10, 1981

[30] Foreign Application Priority Data

Dec. 13, 1980 [DE] Fed. Rep. of Germany ....... 3047106

[51] Int. Cl.³ .................... A61K 7/06; A61K 7/09; A61K 31/36; A61K 31/235
[52] U.S. Cl. ................. 424/70; 424/DIG. 1; 424/DIG. 2; 424/DIG. 4; 424/47; 424/71; 424/72; 424/282; 424/300; 424/304; 424/308; 424/324; 424/358; 424/365; 544/148; 544/173; 544/174; 544/176; 546/270; 546/314; 548/525; 548/540
[58] Field of Search ............ 424/70, DIG. 4, 282, 424/308, 300, 304, 324

[56] References Cited

U.S. PATENT DOCUMENTS

| | | | |
|---|---|---|---|
| 3,422,140 | 1/1969 | Corrodi et al. | 424/324 X |
| 3,510,560 | 5/1970 | Saunders | 424/324 X |
| 3,551,438 | 12/1970 | Oediger et al. | 424/324 X |
| 3,576,869 | 4/1971 | Schellenbaum et al. | 424/324 X |
| 3,711,533 | 1/1973 | Hamilton | 424/308 |

FOREIGN PATENT DOCUMENTS

| | | | |
|---|---|---|---|
| 2223957 | 12/1972 | Fed. Rep. of Germany | 424/304 |
| 18822 | 2/1977 | Japan | 424/320 |
| 28937 | 3/1977 | Japan | 424/304 |
| 358279 | 10/1931 | United Kingdom | 424/304 |

OTHER PUBLICATIONS

Kalish, Advancing Therapy, 8/1967, p. 156, Drug & Cosmetic Industry.
Chem. Abstract, 1979, vol. 90, p. 142165q, Lassman et al., (I).
Chem. Abs., vol. 88, 1978, p. 121010d, Lassman, (II).

*Primary Examiner*—Dale R. Ore
*Attorney, Agent, or Firm*—Hammond & Littel, Weissenberger & Dippert

[57] ABSTRACT

This invention relates to topical cosmetic preparations. More particularly, this invention relates to a topical cosmetic preparation for the treatment of oily hair and seborrheic skin which comprises an effective amount of at least one compound of the formula

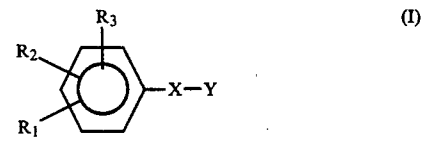

wherein $R_1$, $R_2$, and $R_3$, any of which may be the same or different, each represent hydrogen, hydroxyl, or $-OR_4$, where $R_4$ is an alkyl of from 1 to 6 carbon atoms or a substituted or unsubstituted benzyl, or two of the groups $R_1$, $R_2$, and $R_3$ represent methylenedioxy; X is a substituted or unsubstituted alkylene of from 1 to 3 carbon atoms; and Y is $-COOH$, $-CN$, $-CONR_5R_6$, or $-COOR_7$, where $R_5$ and $R_6$ each represent hydrogen, alkyl of from 1 to 6 carbon atoms, or substituted or unsubstituted aryl, or aralkyl, or together with the nitrogen atom $R_5$ and $R_6$ represent a heterocycle, and $R_7$ is an alkyl of from 1 to 6 carbon atoms or a substituted or unsubstituted aralkyl.

6 Claims, No Drawings

TOPICAL COSMETIC PREPARATIONS FOR THE TREATMENT OF OILY HAIR AND SEBORRHEIC SKIN

FIELD OF THE INVENTION

This invention relates to topical cosmetic preparations. More particularly, this invention relates to topical cosmetic preparations useful in treating oily hair and seborrheic skin.

BACKGROUND OF THE INVENTION

Excessive excretion of the seborrheic glands in the scalp gives hair an oily appearance that generally is considered esthetically unappealing. Consequently, there have been many attempts to make such glands secrete normally by suitable means, to restore a healthy look to the hair. A large number of synthetic products, particularly compounds containing sulfur, have been used to correct these seborrheic conditions, but really satisfactory results with regard to effectiveness or application-technological properties have not yet been obtained. See, for example, U.S. Pat. No. 3,755,604.

OBJECTS OF THE INVENTION

It is an object of the invention to provide topical cosmetic preparations.

It is also an object of this invention to provide topical cosmetic preparations useful in treating oily hair and seborrheic skin.

It is a further object of this invention to provide topical cosmetic preparations comprising compounds of the formula

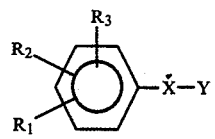

(I)

wherein $R_1$, $R_2$, and $R_3$, any of which may be the same of different, each represent hydrogen, hydroxyl, or —$OR_4$, where $R_4$ is an alkyl of from 1 to 6 carbon atoms or a substituted or unsubstituted benzyl, or two of the groups $R_1$, $R_2$, and $R_3$ represent a methylenedioxy; X is a substituted or unsubstituted alkylene of from 1 to 3 carbon atoms; and Y is —COOH, —CN, —$CONR_5R_6$, or —$COOR_7$, where $R_5$ and $R_6$ each represent hydrogen, alkyl of from 1 to 6 carbon atoms, or substituted or unsubstituted aryl or aralkyl, or together with the nitrogen atom $R_5$ and $R_6$ represent a heterocycle, and $R_7$ is an alkyl of from 1 to 6 carbon atoms or a substituted or unsubstituted aralkyl.

These and other objects of the invention will become more apparent in the discussion below.

DETAILED DESCRIPTION OF THE INVENTION

Applicants have now discovered topical cosmetic preparations which are especially effective in the treatment of seborrheic skin and strongly oily hair. These topical cosmetic preparations contain compounds of the formula

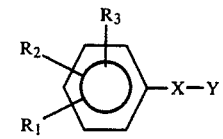

(I)

wherein $R_1$, $R_2$, and $R_3$, any of which may be the same or different, each represent hydrogen, hydroxyl, or —$OR_4$, where $R_4$ is an alkyl of from 1 to 6 carbon atoms or a substituted or unsubstituted benzyl, or two of the groups $R_1$, $R_2$, and $R_3$ represent methylenedioxy; X is a substituted or unsubstituted alkylene of from 1 to 3 carbon atoms; and Y is —COOH, —CN, —$CONR_5R_6$, or —$COOR_7$, where $R_5$ and $R_6$ each represent hydrogen, alkyl of from 1 to 6 carbon atoms, or substituted or unsubstituted hydrocarbon aryl having from 6 to 10 carbon atoms or hydrocarbon aralkyl having from 7 to 11 carbon atoms, or together with the nitrogen atom $R_5$ and $R_6$ represent a heterocyclic ring, and $R_7$ is an alkyl of from 1 to 6 carbon atoms or a substituted or unsubstituted hydrocarbon aralkyl having from 7 to 11 carbon atoms. The benzyl, alkylene, hydrocarbon aryl, and hydrocarbon aralkyl groups can be substituted with one or more non-interfering substituents selected from the group consisting of lower alkyl, halogen, nitro, lower alkanoyl, carboxyl, lower alkoxy, and methylenedioxy.

Preferred compounds of the invention, that is, those which are especially effective, are those in which Y represents —COOH or —$COOR_7$, where $R_7$ is as defined above. Among these, esters of alkoxyphenylalkanoic, dialkoxyphenylalkanoic, and trialkoxyphenylalkanoic acids of the formula

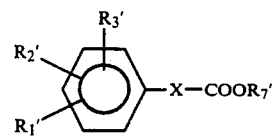

(II)

wherein $R_1'$, $R_2'$, and $R_3'$, any of which may be the same or different, are each hydrogen or —$OR_4'$, where $R_4'$ is an alkyl of from 1 to 6 carbon atoms, at least one of $R_1'$, $R_2'$, and $R_3'$ being —$OR_4'$; X is a substituted or unsubstituted alkylene of from 1 to 3 carbon atoms; and $R_7'$ is an alkyl of from 1 to 6 carbon atoms.

With regard to specific substituents, for example, $R_1$, $R_2$, and/or $R_3$ can be hydroxy, methoxy, ethoxy, or benzyloxy, 3,4-methylenedioxy-benzyloxy; X can be methylene, ethylene, or propylene; $R_5$ and/or $R_6$ can be methyl, ethyl, phenyl, or benzyl, or together with the nitrogen atom $R_5$ and $R_6$ represent a pyridinyl, pyrrolidinyl, or morpholinyl group; and $R_7$ can be methyl, ethyl, or benzyl.

The compounds to be used in the preparations according to the invention are known from the literature, either per se or in the form of their precursors, and are for the most part commercially available. Where only the respective arylalkanoic acids upon which the compounds are based are commercially available, the compounds to be used according to the invention can be prepared simply by generally known methods of organic chemistry. Frequently, the alkoxyarylalkanoic acids will yield the respective hydroxyl compounds by partial or complete demethylation with hydrogen iodide. This preparative method is also suitable for the production of hydroxyarylalkanoic acid amides. The benzyloxy-substituted arylalkanoic acid derivatives are obtained by reacting the hydroxyl-substituted esters with substituted or unsubstituted benzyl halides. Then, the carboxylic acid radical can be modified using well known procedures. Alkoxybenzylacetoacetic acid esters and alkoxybenzylmalonic acid esters can be prepared by alkylating the respective unsubstituted esters with alkoxybenzyl halides. The respective esters, amides, and nitriles can be prepared according to the conventional methods of organic chemistry from the carboxylic acids; however, with respect to arylacetonitrile, the respective benzyl halides are the advantageous starting points to carry out a halogen-cyano exchange.

Suitable arylalkanoic acids upon which the compounds to be used according to the invention are based include, for example, 2-hydroxy-phenylacetic acid, 3-hydroxy-phenylacetic acid, 4-hydroxy-phenylacetic acid, 2-methoxy-phenylacetic acid, 3-methoxy-phenylacetic acid, 4-methoxy-phenylacetic acid, 4-ethoxy-phenylacetic acid, 4-isopropyloxy-phenylacetic acid, 4-hexyloxy-phenylacetic acid, 4-benzyloxy-phenylacetic acid, 4-(3,4-methylenedioxy-benzyloxy)-phenylacetic acid, 2-(p-methoxy-phenyl)-propionic acid, 3-(p-methoxyphenyl)-propionic acid, 2-(p-hydroxyphenyl)-butyric acid, 3-(p-hydroxyphenyl)-butyric acid, 4-(p-hydroxyphenyl)-butyric acid, 4-hydroxy-3-methoxyphenylacetic acid, 2,4-dihydroxy-phenylacetic acid, 2,5-dihydroxy-phenylacetic acid, 3,4-dihydroxyphenylacetic acid, 3,5-dihydroxy-phenylacetic acid, 2,4-dimethoxy-phenylacetic acid, 3,4-dimethoxyphenylacetic acid, 3,4-methylenedioxy-phenylacetic acid, 3-methoxy-4-ethoxyphenylacetic acid, 3-methoxy-4-benzyloxy-phenylacetic acid, 3,4,5-trihydroxyphenylacetic acid, 3,4,5-trimethoxy-phenylacetic acid, 3,4-dimethoxy-mandelic acid, 2-(3,4-dimethoxybenzyl)-acetoacetic acid, 2-(3,4-methylenedioxy-benzyl)acetoacetic acid, 2-(p-methoxyphenyl)-2-methyl-propionic acid, and 3-(3,4-dimethoxyphenyl)-propionic acid.

Alcohol compounds suitable for the preparation of the arylalkanoates to be used according to the invention include, for example, the following: methanol, ethanol, propanol, 2-propanol, butanol, isobutanol, tert.butanol, pentanol, hexanol, benzyl alcohol, 3,4-dimethoxy-benzyl alcohol, 4-chloro-benzyl alcohol, and 3,5-dichloro-benzyl alcohol.

The amine component to be used for the preparation of the hydroxyarylalkanoic acid amides or alkoxyarylalkanoic acid amides according to the invention include, for example, ammonia, methylamine, ethylamine, propylamine, butylamine, hexylamine, dimethylamine, diethylamine, dipropylamine, dibutylamine, benzylamine, 3,4-dimethoxybenzylamine, piperidine, pyrrolidine, and morpholine.

The cosmetic preparations according to the invention are solutions of the active compounds of Formula I, in water, alcohols, aqueous alcoholic mixtures, or oils, suspension in gels, emulsions, ointments, pastes, or aerosols. Principally, almost all cosmetics for the treatment of skin and hair are suitable for the incorporation of the compounds of Formula I, to impart to anti-seborrheic properties by these means. The cosmetic preparations may be in the form of hair lacquers, waving lotions, or hair rinses. Such types of preparations contain, in addition to one or more compounds of the Formula I, present in solution or suspension, surfactants, cellulose derivatives, cationic compounds, vitamins, resins, dyes, and/or perfume oils. The alcoholic or aqueous alcoholic solutions can also be used in admixture with suitable propellants for use in the form of aerosols. Another form of application of the preparations according to the invention is products that are applied to the skin and usually are in the form of cremes, milk preparations, gels, or pastes. In addition to the compounds of Formula I, these products contain as regular components water, solvents, surfactants, oils and fats, waxes, perfume oils, dyes, preservatives, and specific active substances.

The most common form of the preparations according to the invention for the treatment of strongly oily hair is as shampoo. Such shampoos can, in their simplest form, consist of the solution of an anionic, cationic, nonionic, or amphoteric surfactant in combination with a compound of Formula I. Alkyl sulfates, alkyl ether sulfates, alkylsulfonates, sulfated monoglycerides, sulfonated alkanolamides, monosulfosuccinates of fatty alcohols, or condensation products of fatty acids with protein hydrolyzates may, for example, be contained in the shampoos as anionic tensides. Suitable cationic tensides include, for example, long-chain quaternary ammonium compounds, esters of fatty acids, and amino alcohols. Products useful as nonionic tensides in the preparations according to the invention include, for example, sugar esters, esters of polyols, condensation products of ethylene oxide with fatty acids, fatty alcohols, long-chain alkyl-phenols, and long-chain amides. Betaine derivatives and amine oxides are examples of suitable amphoteric tensides. In addition to these components, the shampoos according to the invention may contain the usual cosmetic additives such as thickeners, dyes, fragrances, conditioners, and specific active substances such as anti-dandruff substances. Suitable as thickeners are alkanolamides of fatty acids, carboxymethyl cellulose, hydroxymethyl cellulose, gums, and esters of long-chain polyols.

The cosmetic preparations according to the invention contain the arylalkanoic acid derivatives in an amount of from about 0.01 to 20 percent by weight, preferably from about 1 to 10 percent by weight, based on the weight of the final product. The amounts of other constituents correspond to the amounts customary for such preparations. For example, shampoos may contain the following:

| Component | % by Wt. |
| --- | --- |
| Tensides | about 4 to 20 |
| Thickeners | about 0.1 to 5 |
| Perfuming agents | about 0.5 to 2 |
| Dyes | about 0.01 to 0.1 |
| Preservatives | about 0.1 to 0.2 |

Satisfactory results are obtained with the preparations according to the invention in the final form of a shampoo with one application per week. The oily appearance of the hair is reduced, and the recurrence of oiliness between treatments is reasonable, allowing the possibility of normal hair care.

With the use in the form of cremes, milk preparations, or gels, the appearance of the skin can be permanently considerably improved by regular application to the skin, such as daily or every two days. Satisfactory results can also be achieved in cases of acne, optionally in combined application with conventional acne preparations.

The following examples are intended to illustrate the invention and should not be construed as limiting the invention thereto.

EXAMPLES

First, the preparations and sources of several arylalkane acid derivatives to be used in the cosmetic preparations according to the invention are described.

(A) 3,4-Dihydroxyphenylacetic acid

The preparation of the above compound can be carried out according to the information set forth in the Berichte der deutschen chemischen Gesellschaft 42: 2949, incorporated herein by reference. In the present case, the compound was prepared from the commercially available 3,4-dimethoxyphenylacetic acid. A mixture of 115 gm (587 mmol) of 3,4-dimethoxyphenylacetic acid, 1052 gm (2.35 mol) of 57% hydroiodic acid, and 14 gm of red phosphorus was agitated for 1.5 hours at 95° C. and for an additional 1.5 hours at 105° to 110° C., during which time the calculated amount (166.5 gm) of methyliodide was distilled off. After cooling of the mixture, removal of the red phosphorus by filtration, evaporation of the solution, and taking up of the residue in ether, the ether solution was treated with concentrated $NaHSO_3$ solution and activated charcoal. After drying of the light-yellow solution with $Na_2SO_4$ and evaporation, the residue was suspended in methylene chloride, the residual water was removed by azeotropic distillation, and, after the suspension was cooled, the solid product was removed by suction filtration and dried at 50° C. An amount of 63 gm of 3,4-dihydroxyphenylacetic acid, with a melting point of 126° to 129° C., was obtained (64% of theory).

(B) Ethyl 3,4-dihydroxyphenylacetate

This compound was obtained by esterification of the free acid with ethanol.

$n_D^{20}=1.5268$ (not distilled).

(C) 3,4-Dimethoxyphenylacetic acid

This compound is commercially available. Its preparation is described in Beilstein 10 (II), page 268.

(D) Ethyl 3,4-dimethoxyphenylacetate

This compound was obtained by esterification of the free acid with ethanol. Its analytical data were as follows:

B.p.: 112° C./0.13 mbar
$n_D^{20}=1.5174$

Literature data concerning the compound and its preparation are set forth in J. Chem. Soc. (1959), page 2157.

(E) Methyl 2-(3,4-dimethoxybenzyl)-acetoacetate

This compound can be obtained in a known manner by alkylation of methyl acetoacetate with 3,4-dimethoxybenzyl chloride according to information in Organikum, 8th edition, page 469. The melting point of the compound was 51° C.

(F) Ethyl 4-hydroxyphenylacetate

This compound was obtained by esterification of the free acid with ethanol.

B.p.: 117° C./0.14 mbar
$n_D^{20}=1.5240$

Literature data is set forth in J. Org. Chem. 22 (1957), page 1577.

(G) Ethyl 3-hydroxyphenylacetate

This compound was obtained by esterification of the free acid with ethanol.

B.p.: 111° C./0.16 mbar
$n_D^{20}=1.5236$

Literature data: Diss. Pharm. Pharmacol. 20 (1968), page 607.

(H) 3,4-Dimethoxyphenylacetic acid diethylamide

This compound was obtained by reaction of the acid chloride with diethylamine in ether at room temperature.

B.p.: 144° C./0.08 mbar
$n_D^{20}=1.5342$

Literature data: French Pat. No. 1,336,388

(I) 3,4-Dihydroxyphenylacetic acid diethylamide

This compound was prepared from Compound H using a procedure analogous to that of Compound A, with a yield of 67%.

M.p.: 134° to 137° C.

Literature date: Helv. Chim. Acta 45 (1962), page 270.

(J) Ethyl 3,4-methylenedioxyphenylacetate

This compound was obtained by esterification of the free acid with ethanol.

B.p.: 103° C./0.13 mbar
$n_D^{20}=1.5198$

Literature data: French Pat. No. 1,549,379.

(K) Ethyl 4-(3,4-methylenedioxybenzyloxy)-phenylacetate

To a sodium alcoholate solution of 2.16 gm (94 mmol) of sodium in 100 ml ethanol were added 16.9 gm (94 mmol) of ethyl 4-hydroxyphenylacetate with agitation. Then, 16.0 gm (94 mmol) of 3,4-methylenedioxybenzyl chloride were added dropwise, and the mixture was maintained at the boiling temperature for eight hours. After evaporation, taking up of the residue in ether, washing with $Na_2CO_3$ solution and water, treating of the ether solution with activated charcoal, and evaporation, the residue was distilled at 0.13 mbar. The volatile material that was removed by distillation until a pot temperature of 240° C. was reached, amounted to 5.9 grams. The residue of 21 gm was chromatographed in a column of silica gel (granule size 0.063 to 0.200 mm, available from Merck & Co.), with methylene chloride as solvent. An amount of 16.7 gm of ethyl 4-(3,4-methylenedioxybenzyloxy)-phenylacetate (57% of theory), with a melting point of 49° to 52° C. and refractive index $n_D^{20}=1.5643$, was obtained.

(L) Ethyl 3-(3,4-dimethoxyphenyl)-propionate

This compound was obtained by esterification of the free acid with ethanol.

B.p.: 119° C./0.16 mbar
$n_D^{20}=1.5137$

Literature data: in J. Chem. Soc. (1929), page 2014.

(M) N-[β-(3,4-Dimethoxyphenyl)-ethyl]-3,4-dimethoxyphenyl acetamide

This compound was obtained by the reaction of the acid chloride with β-(3,4-dimethoxyphenyl)-ethylamine in the presence of triethylamine, according to the data in Ber. dtsch. chem. Ges. 42 (1909), page 1986.

M.p.: 122° to 124° C.

(N) N-[β-(3,4-Dimethoxyphenyl)-ethyl]-N-methyl-3,4-dimethoxyphenyl acetamide

This compound was obtained in the form of a yellow oil with the refractive index $n_D^{20}=1.5680$, by methylation of Compound M with methyl iodide.

(O) 3,4-Dimethoxybenzyl 3,4-dimethoxyphenylacetate

This compound was obtained by reaction of the acid chloride with 3,4-dimethoxybenzyl alcohol.

M.p.: 99° to 101° C.

The above-mentioned literature references are incorporated herein by reference.

The anti-seborrheic activity of the compounds used in the cosmetic preparations according to the invention was examined more closely in the animal experiments described hereinafter. The experimental animals were male Wistar rats weighing from 200 to 230 gm. The degree of brown discoloration on the shaved backs of the rats was established visually; the brown discoloration was caused by the brown skin surface lipid of the rats. This test is based on the observation that young female rats as well as male rats that were washed with tenside solution and a lipid solvent, respectively, as well as male rats that were treated with estrogen, show only the normal light, pink skin after shaving; parallel to this, only relatively very small amounts of lipid can be extracted from the cut hair.

For the evaluation of the sebosuppressive activity, test compounds A, B, D, E, G, and H, each in the form of a 1% solution in ethanol or ethanol/acetone (1:1), were each brushed on one side of the back fur of 6 rats. The other side was treated only with the solvent without the active substance (control side). During the testing period of 14 days, application was made once on each of a total of 9 days. A group of 6 rats that remained completely untreated served as an additional control. At the end of the experiment, the animals were shaved on the back and the flanks and inspected visually, independently by an evaluation panel (6 persons) under double-blind conditions.

Three criteria were rated. The first criterion was whether the majority of the evaluators recognized the treated side properly; the differentiations were as follows:

| Symbol | Percentage of evaluators recognizing an effect |
| --- | --- |
| ++ | 100% |
| + | >50% to <100% |
| 0 | ≦50% |

The second criterion was the difference between the right and left side, one point each to be given per evaluator and animal, in the manner that the darker side was rated 1 and the lighter side 0 and that the uniformity of both sides was rated 0.5.

The third criterion was the rating of the difference in intensity of the brown shades on the following scale:

| | |
| --- | --- |
| strong brown | 3 points |
| medium brown | 2 points |
| weakly brown | 1 point |
| no brown color | 0 points |

Significant differences between the untreated and the treated side according to the second method of evaluation indicate the topical effectiveness of a substance. The differences in the point totals between the untreated control animals and the treated and untreated sides, respectively, of the experimental animal group are calculated by the third method of evaluation where significant differences between control animals and the treated side of the experimental animals indicate the effect of a substance. Similarly, a distinct difference between the untreated and the treated side of the experimental animal groups is also generally noticeable. However, this is not always as distinct as that between control animals and treated side, which may be due to various reasons, as for example mechanical transfer of substance from one side to the other or solvent influence. The differentiation of the effects according to the methods of evaluation 2 and 3 was characterized in the following manner:

| Symbol | Difference in points |
| --- | --- |
| ++ | very great (>99.9% probability) |
| + | significant (≧95% probability) |
| (+) | distinct, but <95% probability |

The results of the evaluation according to the above-mentioned scheme for the test substances as set forth in the following table:

TABLE
EVALUATION OF SEBOSUPPRESSIVE EFFECTS

| | Method of Evaluation | | |
| --- | --- | --- | --- |
| Compound | 1 | 2 | 3 |
| A | + | + | + |
| B | 0 | (+) | + |
| D | + | ++ | ++ |
| E | + | (+) | + |
| G | 0 | + | + |
| H | 0 | (+) | + |
| L | + | + | + |
| M | ++ | + | + |
| N | 0 | + | (+) |
| O | + | (+) | + |

Examples of topical cosmetic preparations according to the invention for the treatment of strongly oily hair and seborrheic skin are as follows:

EXAMPLE 1

Skin Emulsion for the Treatment of Oily Skin

| Component | Parts by Weight |
| --- | --- |
| Colloidal dispersion of a mixture of cetylstearyl alcohol, sodium cetylstearyl sulfate, and nonionic emulsifying agent (Emulgade F ®, Dehydag) | 1.00 |
| Mixture of cetylstearyl alcohol and nonionic emulsifying agent (Emulgade F Spec. ®, Dehydag) | 1.00 |
| Decyl oleate | 1.00 |
| Stearic acid | 3.00 |
| Lanolin, anhydrous | 0.50 |
| Glycerin | 1.00 |
| Triethanolamine | 0.25 |
| Compound B | 3.25 |
| Water | 89.00 |
| | 100.00 |

For use of the skin emulsion in aerosol form, 92 parts by weight of the emulsion are filled into an aerosol container with 8 parts by weight of propellant.

EXAMPLE 2

Creme for the Treatment of Oily Skin

| Component | Parts by Weight |
| --- | --- |
| Self-emulsifying mixture of mono-diglycerides on higher saturated fatty acids with potassium stearate (Cutina MD ®, Dehydag) | 16.0 |
| Cetylstearyl alcohol with approximately 12 mols of ethylene oxide | 1.0 |
| 2-Octyldodecanol | 6.0 |
| Isopropyl myristate | 4.0 |
| Glycerin | 6.0 |
| Compound D | 7.0 |
| Water | 60.0 |

-continued

| Component | Parts by Weight |
|---|---|
| | 100.0 |

EXAMPLE 3

Shampoo for Oily Hair

| Component | Parts by Weight |
|---|---|
| Ammonium lauryl sulfate with 33 to 35% by weight of wash active substance | 40.0 |
| Diethanol amide of coconut fatty acids | 3.0 |
| Sodium chloride | 2.0 |
| Sodium sulfate | 2.0 |
| Compound A | 5.5 |
| Preservative | 0.1 |
| Perfume oil | 0.1 |
| Water | 47.3 |
| | 100.0 |

EXAMPLE 4

Shampoo for Oily Hair

| Component | Parts by Weight |
|---|---|
| Triethanolamine lauryl sulfate with 42% by weight of wash active substance | 12.0 |
| Diethanol amide of coconut fatty acids | 2.0 |
| Carboxymethyl cellulose | 0.25 |
| Compound E | 8.25 |
| Perfume oil | 0.2 |
| Water | 77.3 |
| | 100.0 |

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A process of treating oily hair and seborrheic skin which comprises administering to an individual in need of such treatment an effective amount of a topical cosmetic preparation comprising from about 0.01 to 20 percent by weight, based upon the weight of the total preparation, of at least one compound of the formula

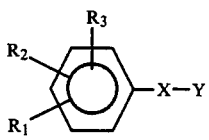

(I)

wherein $R_1$, $R_2$, and $R_3$, any of which may be the same or different, each represent hydrogen, hydroxyl, or —$OR_4$, where $R_4$ is an alkyl of from 1 to 6 carbon atoms or a benzyl, or two of the groups $R_1$, $R_2$, and $R_3$ represent methylenedioxy; X is an alkylene of from 1 to 3 carbon atoms; and Y is —COOH, —$CONR_5R_6$, or —$COOR_7$, where $R_5$ and $R_6$ each represent hydrogen, alkyl of from 1 to 6 carbon atoms, or benzyl and $R_7$ is an alkyl of from 1 to 6 carbon atoms or a benzyl, where each of the benzyl and alkylene may have one or more non-interfering substituents selected from the group consisting of lower alkyl, halogen, nitro, lower alkanoyl, lower alkoxy, and methylenedioxy.

2. The process of claim 1, wherein Y is —COOH or —$COOR_7$, wherein $R_7$ is as defined in claim 1.

3. A process of claim 1, wherein the topical preparation comprises at least one compound of the formula

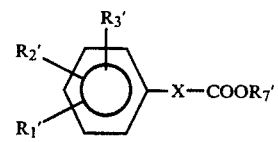

(II)

wherein $R_1'$, $R_2'$, and $R_3'$, any of which may be the same or different, are each hydrogen or —$OR_4'$, where $R_4'$ is an alkyl of from 1 to 6 carbon atoms, at least one of $R_1'$, $R_2'$, and $R_3'$ being —$OR_4'$; X is an alkylene of from 1 to 3 carbon atoms, either unsubstituted or substituted with one or more non-interfering substituents selected from the group consisting of lower alkyl, halogen, nitro, lower alkanoyl, lower alkoxy, and methylenedioxy; and $R_7'$ is an alkyl of from 1 to 6 carbon atoms.

4. The process of claim 1, wherein at least one compound of Formula I is present in an amount of from about 1 to 10 percent by weight, based on the weight of the total preparation.

5. A process for reducing sebaceous cell sebum production in a mammal in need thereof which comprises contacting said sebaceous cell in the skin of said mammal with an effftective amount to reduce sebum production of at least one compound of the formula

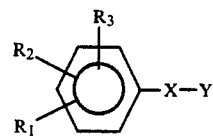

wherein $R_1$, $R_2$, and $R_3$, any of which may be the same or different, each represent hydrogen, hydroxyl, or —$OR_4$, where $R_4$ is an alkyl of from 1 to 6 carbon atoms or a benzyl, or two of the groups of $R_1$, $R_2$, and $R_3$ represent methylenedioxy; X is an alkylene of from 1 to 3 carbon atoms; and Y is —COOH, —$CONR_5R_6$, or —$COOR_7$, where $R_5$ and $R_6$ each represent hydrogen, alkyl of from 1 to 6 carbon atoms, or benzyl and $R_7$ is an alkyl of from 1 to 6 carbon atoms or a benzyl, where each of the benzyl and alkylene may have one or more non-interfering substituents selected from the group consisting of lower alkyl, halogen, nitro, lower alkanoyl, lower alkoxy, and methylenedioxy.

6. A process for reducing sebaceous cell sebum production in a mammal in need thereof which comprises contacting said sebaceous cells in the skin of said mammal with an effective amount to reduce sebum production of at least one compound of the formula

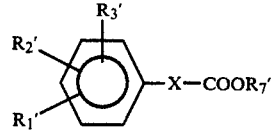

wherein $R_1'$, $R_2'$, and $R_3'$, any of which may be the same or different, are each hydrogen or —$OR_4'$, where $R_4'$ is an alkyl of from 1 to 6 carbon atoms, at least one of $R_1'$, $R_2'$, and $R_3'$ being —$OR_4'$; X is an alkylene of from 1 to 3 carbon atoms, either unsubstituted or or substituted with one or more non-interfering substituents selected from the group consisting of lower alkyl, halogen, nitro, lower alkanoyl, lower alkoxy, and methylenedioxy; and $R_7'$ is an alkyl of from 1 to 6 carbon atoms.

* * * * *